United States Patent [19]

Hureau

[11] Patent Number: Plant 7,566

[45] Date of Patent: Jun. 25, 1991

[54] STRAWBERRY PLANT NAMED DARLINE

[75] Inventor: Robert C. Hureau, Le Vaudoue, France

[73] Assignee: Societe Civile Darbonne, Milly-La-Foret, France

[21] Appl. No.: 407,048

[22] Filed: Sep. 14, 1989

[51] Int. Cl.[5] ..... A01H 5/00

[52] U.S. Cl. ..... Plt./49

[58] Field of Search ..... Plt./48, 49

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct strawberry plant named Darline particularly characterized by its vigorous growth habit, large fruit with firm surface, orange-red fruit color, medium season variety, erect leaves, and its long picking period.

3 Drawing Sheets

The present invention relates to a new and distinctive variety of strawberry plant referred to by the varietal name Darline.

The new cultivar is a product of a planned breeding program. The basic objective of the breeding program was to create a new variety of strawberry having good color, attractive shape, good productivity and good keeping quality.

The new variety was originated from a cross made by the inventor in a controlled breeding program in Milly-La-Foret, France. The female parent was a variety designated Gariguette, and the male parent was a variety designated Aiko.

Darline was discovered and selected by the inventor as a plant within the progeny of the stated cross in a controlled environment in Milly-La-Foret, France. Asexual reproduction of the new variety, as performed by the inventor at Milly-La-Foret, France, has demonstrated that the combination of characteristics as herein disclosed for the new variety are firmly fixed and are retained through successive generations of asexual reproduction. The first selected plant of the variety was asexually propagated by tissue culturing from the cross. The specimens of the variety derived from this tissue culturing were then propagated in a nursery by the production of runners.

Darline has not been observed under all possible environmental conditions. The phenotype may vary significantly with variations in environment. The following observations, measurements and values describe plants grown in Milly-La-Foret, France, under conditions which closely approximate those generally used in commercial practice.

The following traits have been repeatedly observed and are determined to be basic characteristics of Darline, which, in combination, distinguish this strawberry plant as a new and distinct variety:

1. Vigorous growth habit.
2. Erect leaves.
3. Medium season variety.
4. Large sized fruit with firm surface.
5. Orange-red fruit color.
6. Long picking period.
7. Tolerant to Phytophtora Cactorum.

The new variety is most similar to Valeta, being similar thereto in the characteristics of shape and color of the fruit, and distinguishing therefrom in the characteristics of firmness and size. Darline may be distinguished from Darlibelle, Gariguette and Valeta as follows:

| CHARACTERISTICS | DARLINE | DARLIBELLE |
|---|---|---|
| Plant vigor | Vigorous | Very vigorous |
| Leaf habit | Erect | Erect |
| Fruit size | Long and Large | Medium long Medium large |
| Fruit Color | Orange red | Bright red to Purple |
| Fruiting Period | Mid-season | Early to Mid-season |
| Picking duration | 6–7 Weeks | 5–6 Weeks |
| Adaptation to soil | Adapted to all kinds of soils | Adapted to all kinds of soils |
| Tolerance to diseases | tolerant to: Phytophthora Cactorum | tolerant to: Oldium and Botrytis |

| CHARACTERISTICS | GARIGUETTE | VALETA |
|---|---|---|
| Plant vigor | Vigorous | Medium |
| Leaf habit | Less Erect | Less Erect |
| Fruit size | Very long and Medium Large | Large an medium Long |
| Fruit Color | Orange red to orange | Orange red |
| Fruiting Period | Very early | Mid to late season |
| Picking duration | 4–5 Weeks | 4–5 Weeks |
| Adaptation to soil | Needs soil with high clay level | Needs dressing |
| Tolerance to diseases | None | None |

The fruit of Darline is longer than that of Valeta, while the achenes of the fruit of Darline are less prominent than that of Valeta. The fruit of Darline is less glossy at crop time than that of Valeta. The new variety is also similar to Gariguette in the general appearance of its foliage. The leaves of Darline are thicker than of Gariguette, its petioles are stronger and its peduncles are longer than those of Gariguette.

The accompanying color photographic drawings show fruit and foliage from specimen plants of the new variety.

Sheet 1 is a color photograph of a bed of plants of the new variety.

Sheet 2 is a color photograph showing several whole berries, and two berries sectioned to show flesh formation and color.

Sheet 3 is a color photograph showing in plan view and in actual size typical leaves of Darline. The colors appearing in the photographs are as true as possible with color illustrations of this type.

In the following description, color references are made to The Royal Horticultural Society Colour Chart, or to Pantone Matching System 747XR, or where ordinary dictionary terms are used.

Parentage:

*Male parent.*—Aiko.

*Female parent.*—Gariguette.

Propagation: Good production of runners. Darline is late rooting and produces a big plant. When planted in a nursery in March, Darline will produce from 60–80 runners the following November. The diameters of the runners at ground surface vary from 6–10 millimeters. These runers are less vigorous than those of Gariguette.

PLANTS

A. Overall size: Large globose, with a medium to dense density.

B. General plant habit:

1. *Preferred planting.*—In Milly-La-Foret, France is early July, with peak production occurring in June.
2. *Plant habit.*—Globose.
3. *Plant density.*—Medium to dense.
4. *Plant vigor.*—Strong.

C. Leaves:

1. *Size.*—Medium, with mature leaves being approximately 7–11 cm long and 6–10 cm wide, smaller than those of Gariguette but similar in size to those of Darlibelle.
2. *Shape.*—Longer than broad, edges serrated and slightly concave.
3. *Color.*—Upper surface, light green, approximately 137B-C. The adult leaves possess a similar green to that of Gariguette, but a lighter green than that of Darlibelle. The adult leaves are green at the bottom, and lighter green at the top.
4. *Growth habit.*—3 leaflets, the same as Gariguette and Darlibelle; more upright than Gariguette and similar to Darlibelle.
5. *Leaf cross section.*—Slightly concave.
6. *Leaf blistering.*—Medium, shape less blistering than that of Gariguette or Darlibelle.
7. *Terminal leaflet.*—Longer than broad. a. Shape of base: acute. b. Shape of tip: obtuse.
8. *Petiole.*—Position of hairs — upward; as long as those of Gariguette, but shorter than Darlibelle (250 to 380 millimeters with a diameter of 4 to 4.5 millimeters).
9. *Stipule anthocyanin coloration.*—Medium anthocyanin coloration, less than that of Gariguette or Darlibelle.
10. *Stolons.*—Numerous. a. Anthocyanin coloration — medium. b. Thickness — medium to thick. c. Pubescence — medium.

INFLORESCENCE

A. Size and shape: Large, free medium to large petals; slightly obtuse and bigger than those of either Gariguette or Darlibelle.

B. Peduncles: Medium to large size, bigger than those of either Gariguette or Darlibelle.

C. Pedicel origination and form, and characteristics of hair: Large and long pedicel with 1 or 2 upward hairs.

D. Abundance: Medium density, less than Darlibelle or Gariguette. Darline will produce 40–50 flowers per plant.

E. Color: Typical.

F. Anthers and pollen production: Good production similar to Gariguette.

G. Calyx size, and sepal form and color: Calyx larger than corolla; acute and light green colored sepal.

H. Position relative to foliage: Beneath.

I. Flower size: Large.

J. Size of calyx relative to corolla: Same size.

K. Size of inner calyx relative to outer: Larger.

L. Spacing of petals (on flowers with 5 or more petals): Free.

M. Petal length/width ratio: Broader than long.

N. Time of flowering (50% of plants at first flower): Medium.

FRUIT

A. Overall size and shape (primary and secondary fruit): Primary fruits: large, (larger than those of Darlibelle or Gariguette), conical to almost cylindrical, weighing 25–40 grams. Production starts in the third week of April. Secondary fruits: similar in shape to the primary fruits but smaller, 18–28 grams, much bigger and shorter than those of Gariguette. Fruits of Darline are longer than those of Darlibelle.

B. Seed characteristics: Below surface.

C. Juiciness: Juicy.

D. Taste: Medium sweetness and acidity, sweeter and less acid than those of Gariguette.

E. Color: Exterior orange-red, and flesh variable from near white to orange-red toward surface.

F. Exterior surface: The orange red is similar to that of Valeta, but possesses less orange than does Gariguette and less red than does Darlibelle; the fruit is a blend of 171 C (PMS), warm red, yellow and trans. white, and 172 C (PMS), warm red and yellow.

1. *Glossy.*—Strong not as strong as Darlibelle or Gariguette.
2. *Shape.*—Conical shorter than Gariguette, but longer than Darlibelle.
3. *Firmness.*—Firm not as firm as Gariguette or Darlibelle.

G. Characteristics of flesh and core: Firm and juicy, less juicy than Darlibelle; medium large white core, which is less visible than Darlibelle but similar to Gariguette.

H. Keeping qualities: Remains glossy and firm for over four days, after cooling, in a temperature of 10° C. without rotting. Slightly less resistant to bruising than Darlibelle. Keeps its orange-red color during storage. Glossiness decreases slightly during storage.

I. Time of ripening (50% of plants): Medium.

J. Fruit bearing habit: Partially remontant.

K. Fruiting truss: Attitude at first picking, prostrate.

L. Fruit ratio of length/max width: Longer than broad.

M. Predominant shape of fruit: Conical to almost cylindrical; longer than wide.

N. Difference in shape between primary and secondary fruits: Moderate.

O. Band without achenes (seeds): Medium.

P. Unevenness of surface: Weak to medium.

Q. Evenness of color: Even.

R. Glossiness: Strong.

S. Insertion of achenes (seeds): Below surface.

T. Insertion of calyx: Level to setting above fruit.

U. Position of the calyx segments: Clasping or attached.

V. Size of calyx in relation to fruit diameter: Larger.

W. Adherence of calyx: Strong.

X. Aroma: Primary fruits possess a weak aroma, weaker than that of Gariguette, but similar to that of Darlibelle. The secondary fruits have a sharper aroma than do the primary fruits, possessing less aroma than that of Gariguette but more than that of Darlibelle.

Disease tolerant: Resistance to Oidium; tolerant to Phytophtora-Cactorum.

General observations: Darline is less affected by soil deficiencies than most commercial varieties, but will reduce its fruit production in an excess of nitrogen. Darline is, in this way, similar to Darlibelle. The fruit of Darline will remain very attractive on the market, as will Darlibelle's fruit, but will not darken during storage. These traits make the variety distinguishable from most commercial varieties.

I claim:

1. A new variety of strawberry plant named Darline, as illustrated and described.

* * * * *

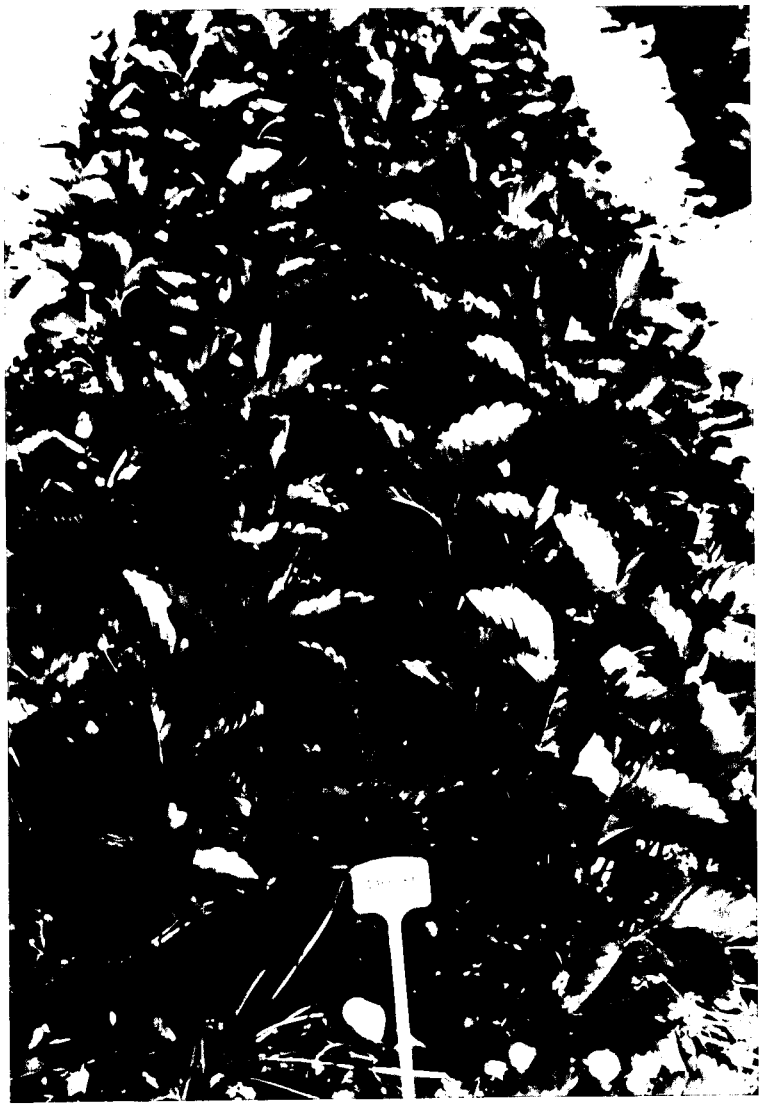

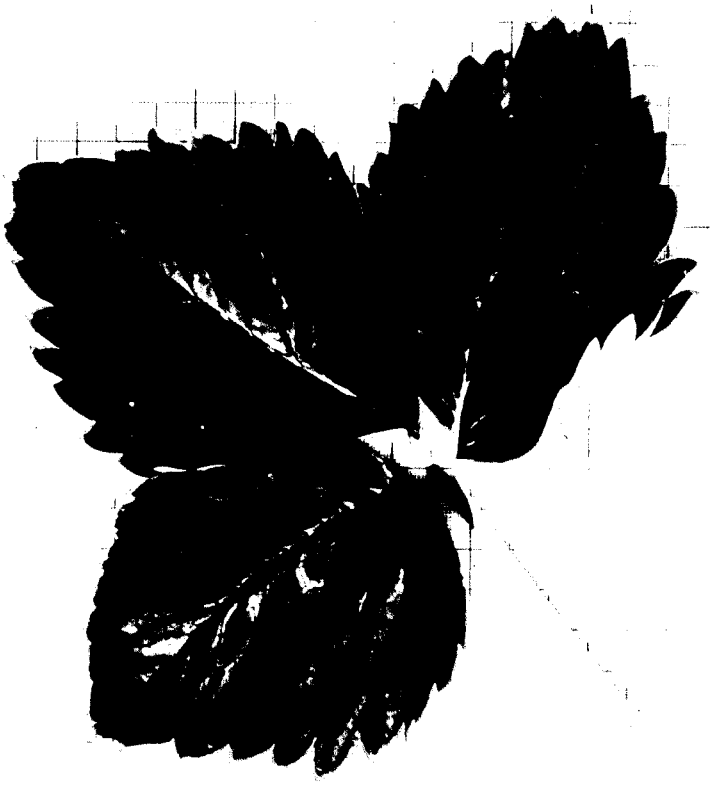

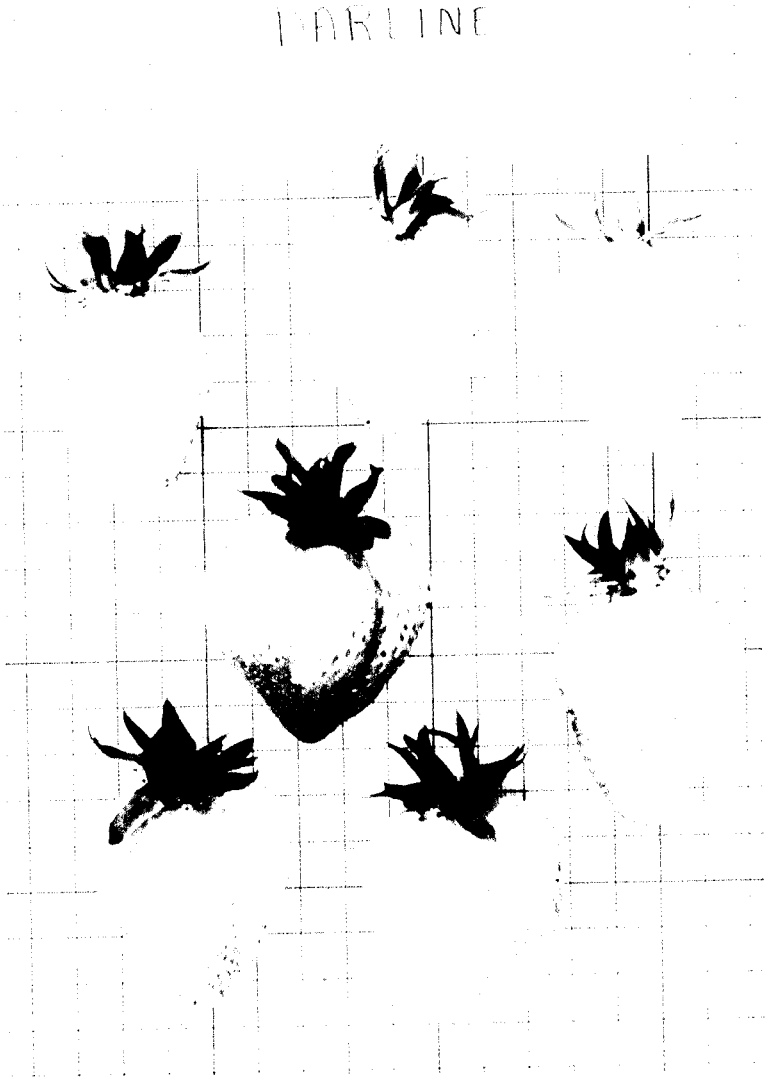
MARLINE